United States Patent [19]

Nakagawa et al.

[11] Patent Number: 4,822,879
[45] Date of Patent: Apr. 18, 1989

[54] ENZYME-INHIBITORY GRISEOLIC ACID DERIVATIVES, AND THEIR USE

[75] Inventors: Fumio Nakagawa; Yoshio Tsujita; Mitsuo Yamazaki, all of Hiromachi, Japan

[73] Assignee: Sankyo Company Limited, Tokyo, Japan

[21] Appl. No.: 131,438

[22] Filed: Dec. 11, 1987

Related U.S. Application Data

[63] Continuation of Ser. No. 734,868, May 16, 1985, abandoned.

[30] Foreign Application Priority Data

May 22, 1984 [JP] Japan ................. 59-102993

[51] Int. Cl.$^4$ ................. C07D 19/40; C07H 17/02
[52] U.S. Cl. ................. 544/277; 435/119; 536/22; 536/26
[58] Field of Search ............ 536/22; 435/119; 544/277, 276

[56] References Cited

U.S. PATENT DOCUMENTS 4,460,765  7/1984  Naito et al. ................. 544/277

Primary Examiner—Nicholas S. Rizzo
Attorney, Agent, or Firm—Frishauf, Holtz, Goodman & Woodward

[57] ABSTRACT

Dihydrodesoxygriseolic acid, which has the formula

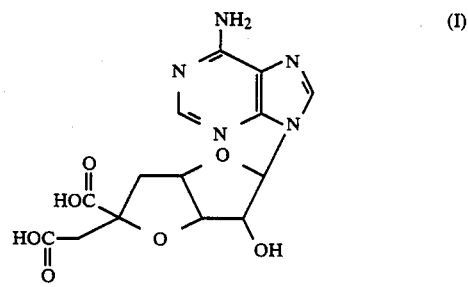

and salts and esters thereof may be prepared by cultivating a suitable strain of Streptomyces, e.g. *Streptomyces griseoaurantiacus* No. 43894, and, if necessary, salifying or esterifying the free acid. These compounds inhibit the activity of various cyclic nucleotide phosphodiesterases, particularly cAMP PDE, and, as a result of this, have a variety of physiological activities and uses.

8 Claims, 4 Drawing Sheets

ENZYME-INHIBITORY GRISEOLIC ACID DERIVATIVES, AND THEIR USE

This is a continuation of application Ser. No. 734,868, filed May 16, 1985, now abandoned.

BACKGROUND TO THE INVENTION

The present invention relates to a novel griseolic acid derivative, named "dihydrodesoxygriseolic acid", as well as salts and esters of this acid.

Griseolic acid is a nucleoside-type compound having an adenine base and two carboxylic acid groups. It was first disclosed in, inter alia, European patent specification No. 29,329A, but its structure was not, at that stage, known. Its structure was first disclosed in U.S. Pat. No. 4,460,765 (assigned to the present assignees). Certain derivatives of griseolic acid were subsequently disclosed in U.S. patent application Ser. No. 664,866 which issued as U.S. Pat. No. 4,634,706 assigned to the present assignees. U.S. Pat. No. 4,634,706 also discloses the structure of griseolic acid. In accordance with the recommendations of the International Union of Pure and Applied Chemistry (IUPAC), the compounds of the present invention are named as derivatives of griseolic acid, taking griseolic acid as the parent structure. The numbering system employed is shown in U.S. Ser. No. 664,866.

Griseolic acid and the griseolic acid derivatives of U.S. Ser. No. 664,866, as well as the derivatives of the present invention, have the ability to inhibit the activity of phosphodiesterases specific to various cyclic nucleotides, for example 3',5'-cyclic adenosine monophosphate (cAMP) phosphodiesterase (PDE) or 3',5'-cyclic guanosine monophosphate (cGMP) PDE, and can thus increase the level of the cyclic nucleotide, e.g. cAMP or cGMP, in the cells of a patient treated with such a compound.

It is well known that cAMP, which is very widely distributed in animal tissues, functions as a second messenger for and mediates the effect of a large number of hormones; as a result, cAMP has a variety of very important physiological and biochemical roles. Additionally, it is known to have an effect on or participate in: division, proliferation and differentiation of cells; the systolic system, particularly miocardia; haematopoiesis; various activities of the central nervous system; immune reactions; and the liberation of insulin and histamine. Its concentration in tissues, and hence its effect upon these various functions, depends upon the balance between the enzyme which synthesizes cAMP (i.e. adenylate cyclase) and the enzyme which decomposes cAMP, cAMP PDE. An inhibitor against cAMP PDE would increase the level of cAMP in the cells and is thus expected to have a variety of therapeutic uses, for example: in the treatment of cardiovascular problems; as an antiasthmatic agent; as a smooth muscle relaxant; as a psychotropic or neurotropic agent; as an anti-inflammatory agent; in the therapy of cancer; and as a treatment for diabetes.

Other cyclic nucleotides are believed to have a similar range of activities and, hence, inhibitors of PDE's which decompose them would have a similar range of effects.

We have now discovered a compound which is related to griseolic acid and which shares the activity of griseolic acid, but which has a surprisingly low toxicity, leading to the possibility of wider and more effective use.

BRIEF SUMMARY OF INVENTION

It is an object of the present invention to provide, as a new composition of matter, a derivative of griseolic acid and salts and esters thereof.

It is a further, and more specific, object of the invention to provide a derivative of griseolic acid which retains the ability to inhibit the activity of PDE's which decompose cyclic nucleotides, e.g. cAMP PDE or cGMP PDE, but which has significantly lower toxicity than griseolic acid itself.

It is a further object of the invention to provide for the preparation of the compound by isolation from a culture of a suitable microorganism of the genus Streptomyces.

The compounds of the present invention are dihydrodesoxygriseolic acid and salts and esters thereof.

Dihydrodesoxygriseolic acid and salts thereof may be prepared by cultivating a dihydrodesoxygriseolic acid-producing microorganism of the genus Streptomyces in a culture medium therefor and separating dihydrodesoxygriseolic acid or a salt thereof from the culture medium. The esters may be prepared by conventional esterification procedures commencing with the free acid or salt.

DETAILED DESCRIPTION OF INVENTION

Figure 1:
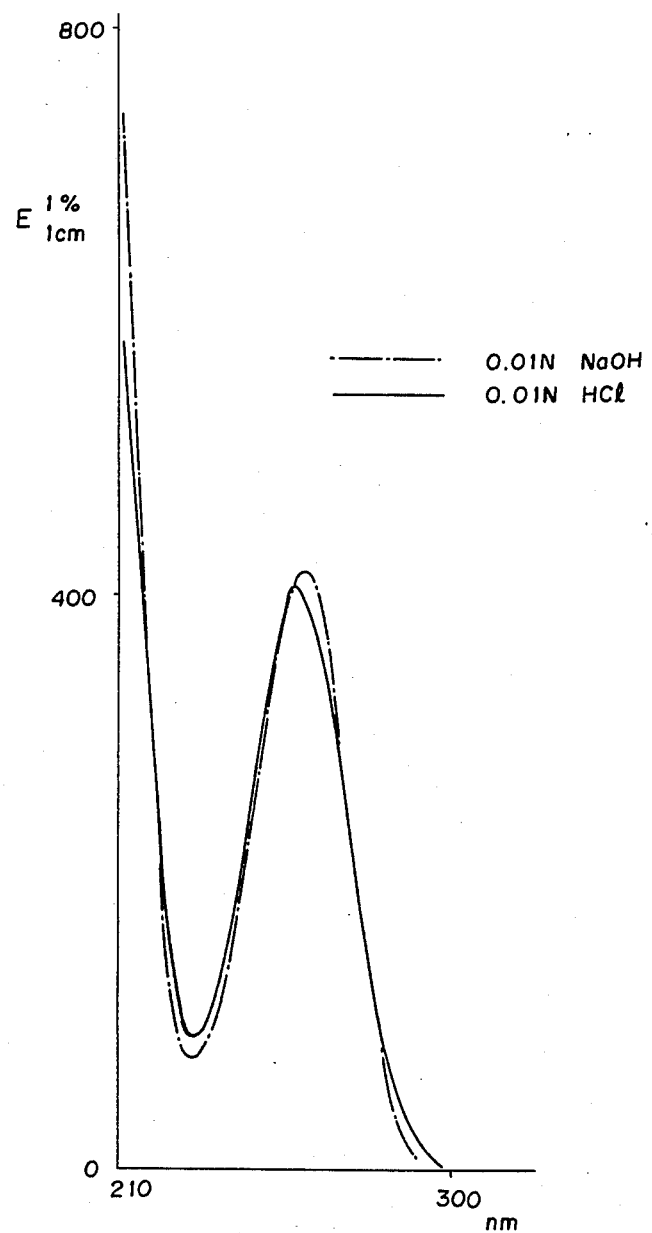
FIG. 1 shows the ultraviolet absorption spectrum of dihydrodesoxygriseolic acid (see Example 1).

The structural formula of dihydrodesoxygriseolic acid has been found to be:

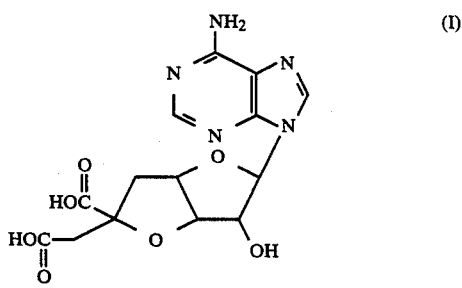

(I)

This compound contains a number of asymmetric carbon atoms, leading to the possibility of a variety of optical isomers and diastereoisomers. However, biological production of such compounds is usually stereospecific and it is believed that the isomer of dihydrodesoxygriseolic acid produced by fermentation in accordance with the process of the present invention has the configuration:

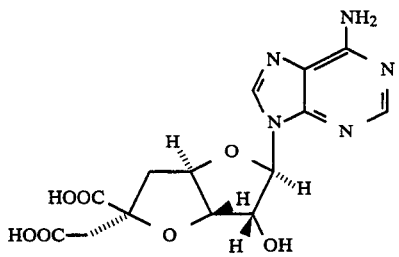
(II)

Dihydrodesoxygriseolic acid and salts thereof may be produced by cultivating an appropriate microorganism of the genus Streptomyces in a culture medium therefor and then separating the active product from the culture broth. The microorganism is preferably a strain of the species *Streptomyces griseoaurantiacus*, more preferably *Streptomyces griseoaurantiacus* No. 43894 (FERM-P 5223). *Streptomyces griseoaurantiacus* No. 43894 is the same strain as is disclosed in European patent publication No. 29,329A and U.S. Pat. No. 4,460,765 as *Streptomyces griseoaurantiacus* SANK 63479. It was deposited on 9th October 1979 at the Fermentation Research Institute, Agency of Industrial Science and Technology, Japan, whence it is available under the accession No. FERM-P 5223, and on 22nd October 1980 at the Agricultural Research Service, Peoria, U.S.A. whence it is available under the accession No. NRRL 12314. Full details of the characteristics of *Streptomyces griseoaurantiacus* No. 43894 are given in European patent publication No. 29,329A and in U.S. Pat. No. 4,460,765.

As is well known, the properties of Actinomycetes, including Streptomyces, strains are not fixed and they readily undergo mutation both through natural causes and as a result of artificial mutation. Although the present invention describes the production of dihydrodesoxygriseolic acid and its salts principally by the cultivation of the above-identified *Streptomyces griseoaurantiacus* No. 43894, it also includes within its scope the use of mutants of this organism and generally of any Streptomyces strain which is capable of producing dihydrodesoxygriseolic acid and its salts.

The cultivation of the dihydrodesoxygriseolic acid-producing microorganism, in accordance with the process of the present invention, can be performed under the conditions conventionally employed for the cultivation of Actinomycetes strains, commonly in an aqueous medium.

The nutrient medium used for the cultivation in the process of the invention can be any composition conventionally used for the cultivation of Actinomycetes and, as such, would include at least an assimilable carbon source and an assimilable nitrogen source. Examples of suitable assimilable carbon sources include: a concentrated solution of a sugar (e.g. of sucrose and/or invert sugar or of a mixture of sucrose with another sugar, such as glucose), corn syrup, starch, glucose, mannitol, fructose, galactose or rhamnose or any combination of two or more thereof. Examples of suitable nitrogen sources, which may be organic or inorganic, include: ammonium salts, such as ammonium chloride, ammonium sulfate or ammonium nitrate; other inorganic nitrogen compounds, such as sodium nitrate; organic nitrogen compounds, such as urea; and nitrogen-containing natural products, such as peptone, meat extract, yeast extract, dried yeast, live yeast, corn steep liquor, soybean meal, soybean flour, casamino acid or soluble vegetable proteins. A single such nitrogen source or a combination of any two or more thereof may be employed. In addition, the nutrient medium may also contain inorganic salts (such as sodium chloride, potassium chloride, calcium carbonate, magnesium chloride or phosphoric acid salts) and may optionally also contain other organic or inorganic substances to promote the growth of the microorganism or its production of dihydrodesoxygriseolic acid and/or a salt thereof.

In particular, since dihydrodesoxygriseolic acid has two carboxylic acid groups and one amino group within its molecule, it forms salts. By including an inorganic salt (particularly an alkali metal salt such as sodium chloride or potassium chloride, or an alkaline earth metal salt, such as calcium carbonate or magnesium chloride) in the culture medium, it is possible to predispose the fermentation product to be obtained in the form of the corresponding alkali metal (e.g. sodium or potassium) or alkaline earth metal (e.g. calcium or magnesium) salt.

The method of cultivation may be freely chosen from the well-known methods employed for the cultivation of Streptomyces and other Actinomycetes strains; for example suitable cultivation techniques include reciprocal shaking cultivation, rotatory shaking liquid cultivation, solid cultivation and deep stirring cultivation, preferably deep stirring cultivation. Although the microorganism will proliferate over a wide range of temperatures, it is particularly preferred to effect the cultivation at a temperature of from 20° to 35° C. and at a substantially neutral pH value, typically a pH value of from 6 to 8. When a liquid cultivation method is employed, the cultivation is normally effected for a period of from 48 hours to 120 hours, during which time dihydrodesoxygriseolic acid and/or a salt thereof (and normally also griseolic acid and/or a salt thereof) is formed and accumulates in the culture broth. The progress of the cultivation may be monitored and the content of active compound in the broth estimated by determining the enzyme inhibitory activity of the broth, for example using the method described in more detail in Example 5 hereafter. After completion of deep liquid cultivation, the culture broth will generally show an inhibitory activity of from 70 to 85%.

Dihydrodesoxygriseolic acid is related to griseolic acid by the conversion of the hydroxy group at the 7'-position of griseolic acid to a hydrogen atom and by the hydrogenation of the double bond between the 4'- and 5'-positions of griseolic acid. Accordingly, it may also be produced semi-synthetically by treatment of griseolic acid with a reducing agent. The nature of the reducing agent is not critical, provided that it does not, or does not to an unacceptable extent, affect other parts of the molecule. Examples of suitable reducing agents are well known to those skilled in the art. The reaction conditions will vary depending on the nature of the reducing agent, but these are also well known to the man skilled in the art and require no elucidation here.

Dihydrodesoxygriseolic acid is an acidic, water-soluble substance. It is, therefore, possible to employ methods of separation and purification of the type commonly used for the isolation of water-soluble microorganism metabolic products from an aqueous culture broth. In the case of the deep stirring cultivation method, the preferred separation and purification procedure is as follows. First, the mycellia are separated by filtration or centrifugation and the resulting filter cake is washed with water. The washings and the filtrate or supernatant liquor from the centrifugation are combined and the combined liquor is treated, in turn, with activated charcoal or another adsorbent and with an ion-exchange resin having an affinity for dihydrodesoxygriseolic acid or a salt thereof. The adsorption may be conducted either batchwise or by continuously feeding the liquor through an adsorption column. In the batch method, for example, activated charcoal or another adsorbent is preferably added in an amount of from 0.1 to 0.6% w/v, more preferably from 0.35 to 0.40% w/v, to the filtrate, and the resulting mixture is stirred for a period of from 30 to 60 minutes. The activated charcoal or other adsorbent is then eluted, for example with aqueous acetone or an aqueous lower alkanol, and the eluate is concentrated by evaporation under reduced pressure. The residue is then further purified by a second adsorption and elution procedure, for example with an ion-exchange resin, such as Diaion (trademark) or Sephadex (trademark), or activated charcoal, to give the pure dihydrodesoxygriseolic acid or salt thereof.

Where the product of the above process is dihydrodesoxygriseolic acid, it may be converted to a salt by conventional means. For example, one suitable salification technique comprises: dissolving the dihydrodesoxygriseolic acid in a small amount of water or of an aqueous organic solvent (such as a mixture of water and ethyl acetate); adding to the resulting solution a solution of an appropriate alkaline compound of the cation whose salt is to be formed, for example, where the salt to be formed is a salt of an alkali metal (e.g. sodium or potassium) or of an alkaline earth metal (e.g. calcium or magnesium), using a hydroxide, carbonate or bicarbonate of the metal; then, if necessary, adjusting the pH of the reaction mixture to a neutral or alkaline value, e.g. a value of from 7 to 10; and, finally, filtering off the resulting precipitate to give the desired salt. This may, if necessary, be subjected to purification by, for example, the various chromatography techniques, particularly column chromatography, to give a pure product.

The compounds of the invention may also be converted to appropriate esters by conventional esterification techniques. The nature of the ester produced is not critical and the only criterion is that, where the compound is to be employed for therapeutic use, the ester should be "pharmaceutically acceptable", which, to those skilled in the art, means that the ester must not, or must not to an unacceptable extent, either reduce the activity or increase the toxicity of the compound as compared with the free acid. Examples of suitable esters include: $C_1$–$C_6$ alkyl esters, particularly the methyl, ethyl, propyl, isopropyl, butyl, isobutyl, sec-butyl, t-butyl, pentyl, isopentyl, neopentyl, t-pentyl and hexyl esters, most preferably the methyl and ethyl esters; aralkyl esters, in which the aryl part is a $C_6$–$C_{14}$ carbocyclic aromatic group, more preferably a $C_6$–$C_{10}$ group and most preferably a phenyl, 1-naphthyl or 2-naphthyl group, and the alkyl part is a $C_1$–$C_6$, more preferably $C_1$–$C_3$, alkyl group, for example the benzyl, phenethyl, 3-phenylpropyl, 1-naphthylmethyl and 2-naphthylmethyl esters; diarylalkyl esters, in which the aryl and alkyl parts are both as defined above in relation to aralkyl esters, preferably the benzhydryl esters; aliphatic acyloxyalkyl esters, in which the aliphatic acyl group is a $C_1$–$C_7$, preferably $C_2$–$C_5$, aliphatic acyl group which may be saturated or unsaturated (preferably saturated) and the alkyl part is a $C_1$–$C_6$, more preferably $C_1$–$C_4$ and most preferably $C_1$ or $C_2$, alkyl group, for example the acetoxymethyl, propionyloxymethyl, butyryloxymethyl, pivaloyloxymethyl, 1-acetoxyethyl, 1-propionyloxyethyl, 1-butyryloxyethyl, 1-pivaloyloxyethyl, 1-acetoxypropyl, 1-propionyloxypropyl, 1-butyryloxypropyl and 1-pivaloyloxypropyl esters; alkoxycarbonyloxyethyl esters in which the alkoxy part is a $C_1$–$C_4$ alkoxy group, and preferably the 1-alkoxycarbonyloxyethyl esters, for example the 1-methoxycarbonyloxyethyl, 1-ethoxycarbonyloxyethyl, 1-propoxycarbonyloxyethyl, 1-isopropoxycarbonyloxyethyl, 1-butoxycarbonyloxyethyl and 1-isobutoxycarbonyloxyethyl esters; heterocyclic esters in which the heterocyclic group (which may be a monocyclic or fused polycyclic, preferably bicyclic, ring system) has from 5 to 14 ring atoms, of which from 1 to 5 are hetero-atoms selected from the group consisting of nitrogen, oxygen and sulfur atoms, such as the phthalidyl esters; and heterocyclylmethyl esters, in which the heterocyclic group has from 5 to 14 ring atoms, of which from 1 to 5 are hetero-atoms selected from the group consisting of nitrogen, oxygen and sulfur atoms, and which may optionally have from 1 to 3 substituents selected from the group consisting of $C_1$–$C_6$ alkyl groups and oxo groups, for example the 5-methyl-2-oxo-1,3-dioxolen-4-ylmethyl esters.

Preparation of the ester may be effected by conventional means, the precise details of reagents and reaction conditions depending upon the nature of the ester which it is desired to prepare.

For example, to form a benzhydryl ester, dihydrodesoxygriseolic acid is reacted with diphenyldiazomethane. The reaction is preferably effected in the presence of a solvent, the nature of which is not critical, provided that it has no adverse effect upon the reaction. The preferred solvent is aqueous acetone. The reaction may be carried out over a wide range of temperatures, but, for convenience, we normally prefer to carry out the reaction at a temperature within the range from 0° to 100° C. and more preferably at about ambient temperature. The time required for the reaction will vary, depending upon the reaction conditions, principally the reaction temperature, but a period of from 15 to 24 hours will normally suffice.

Preparation of a methyl ester is preferably effected by reacting dihydrodesoxygriseolic acid with diazomethane, trimethylsilyldiazomethane or 1-methyl-3-p-tolyltriazene. The reaction is preferably effected in the presence of a solvent, the nature of which is not critical, provided that it has no adverse effect upon the reaction and that it dissolves the starting materials, at least to some degree; aqueous acetone or aqueous dimethylformamide are preferred. The reaction temperature is not particularly critical and a temperature of from 0° C. to ambient temperature is preferred. The time required for the reaction will vary, depending upon the nature of the reagents, and upon the reaction temperature. However, a period of from 1 to 10 hours will normally suffice.

Lower alkyl esters (e.g. $C_1$–$C_4$ alkyl esters, such as the methyl, ethyl, propyl, isopropyl, butyl, isobutyl, sec-butyl and t-butyl esters) in which the alkyl group is optionally substituted may be prepared by reacting dihydrodesoxygriseolic acid with an active ester. The active ester will normally be prepared by reacting a lower alcohol (such as methanol, ethanol or propanol, or other alcohol whose ester it is desired to prepare)

with a conventional reagent, such as benzoyl chloride or ethyl chloroformate. The reaction is preferably effected in the presence of a solvent, the nature of which is not critical, provided that it has no adverse effect upon (although it may participate in) the reaction. In general, we prefer to employ as the solvent the alcohol whose ester is to be prepared. The reaction temperature is not particularly critical and may suitably be in the range of from −20° C. to +100° C.; however, in order to avoid side reactions, a temperature towards the lower part of this range, for example a temperature of from −10° C. to ambient temperature, is preferred. The time required for the reaction will vary, depending upon the nature of the reagents and on the reaction temperature. For example, where the reaction is carried out at ambient temperature, it will normally require about 15 hours.

The demonstrated in vitro activity of the compounds of the invention suggests that they will be of value in the treatment of various disorders arising from a deficiency of cyclic nucleotides, most notably cAMP, in the cells and blood and, in particular, that they will be of value in the therapy of various disorders of the cerebral circulatory system (for example in the treatment of the sequelae of cerebral apoplexy or cerebral infarction), as activators for the cerebral metabolism (e.g. in the therapy of presbyophrenia) and in the treatment of traumatic brain infarction. The compounds of the invention may be administered orally or parenterally (for example by subcutaneous or intramuscular injection).

For administration, the compounds of the invention are preferably formuated in conventional pharmaceutical dosage forms, the nature of which will depend upon the dose, target patients and route of administration. For example, for oral administration, the compounds may be formulated as solid preparations, for example, tablets, capsules, granules or powders, or as liquid preparations, such as syrups or elixirs, and may, if necessary, contain various conventional pharmaceutical additives or adjuvants. Such additives and adjuvants include: diluents, such as sugars and cellulose preparations; binders, such as starch, gums and methylcellulose; and disintegrating agents.

The dosage will vary depending upon the symptoms and severity of the disorder, and the age, condition and body weight of the patient but, for example, in the case of an adult human patient, a suitable daily dose is expected to be from 0.1 to 100 mg of active compound, which may be administered in a single dose or in divided doses.

The preparation and activity of compounds of the present invention are illustrated by the following non-limiting Examples.

EXAMPLE 1

Dihydrodesoxygriseolic Acid 30 liters of a medium having a pH of 7.0 before sterilization and the following composition (percentages are w/v) were prepared:
Glucose 5%
Soybean Meal 1%
Yeast Extract 0.1%
Polypeptone 0.4%
Meat Extract 0.4%
Sodium Chloride 0.25%
Calcium Carbonate 0.5%
Water to 100%

15 liters of this medium were charged into each of two 30 liters jar fermenters, which were then sterilized under pressure at 120° C. for 30 minutes. The culture medium was cooled, and then 150 ml (1% by volume) of a culture broth of *Streptomyces griseoaurantiacus* No. 43894 (which had previously been incubated in the medium described above by means of a rotatory shaking cultivator at 28° C. for 72 hours) were inoculated into each fermenter. Cultivation was then carried out at 28° C. for 96 hours under aeration at the rate of 15 liters per minute and with agitation at the rate of 200 rpm.

The two culture broths were then filtered to remove the mycelial cake and the combined filtrates (pH 7.0), in a total volume of 28 liters, were passed through a column of Diaion HP 20 (a trademark for an ion-exchange resin produced by Mitsubishi Chemical Industries Ltd.) and then adsorbed on a column of activated charcoal. This column was washed with water and then the adsorbed material was eluted with a 60:40 by volume mixture of acetone and water. The acetone was evaporaed from the resulting solution under reduced pressure and the remaining aqueous solution was concentrated by evaporation under reduced pressure and then lyophilized, to give 150 mg of a crude powder.

This crude powder was dissolved in a small amount of distilled water and then adsorbed on Dowex 1×4 (Cl$^-$ form, a trademark for an ion-exchange resin produced by the Dow Chemical Company). At this stage, the product was a mixture of griseolic acid and dihydrodesoxygriseolic acid. This mixture was subjected to gradient elution with a sodium chloride gradient to separate the two components and then the eluate was subjected to column chromatography through Sephadex LH-20 (a trademark for a product of Pharmacia Co) and the dihydrodesoxygriseolic acid was eluted with water. The fractions containing this substance were combined and their pH was adjusted to a value of 2.5 by the addition of 1N aqueous hydrochloric acid. The product was then adsorbed on a column of Diaion HP 20, washed with water and then eluted with a 60:40 by volume mixture of acetone and water. The eluate was left to stand overnight at 4° C., whereupon the dihydrodesoxygriseolic acid separated out as plates. These were separated from the liquor, giving a total of 1.87 mg of dihydrodesoxygriseolic acid. This compound gave a single spot on silica gel thin layer chromatography (silica gel Art. 5715, a product of Merck & Co. Inc.).

Figure 2:
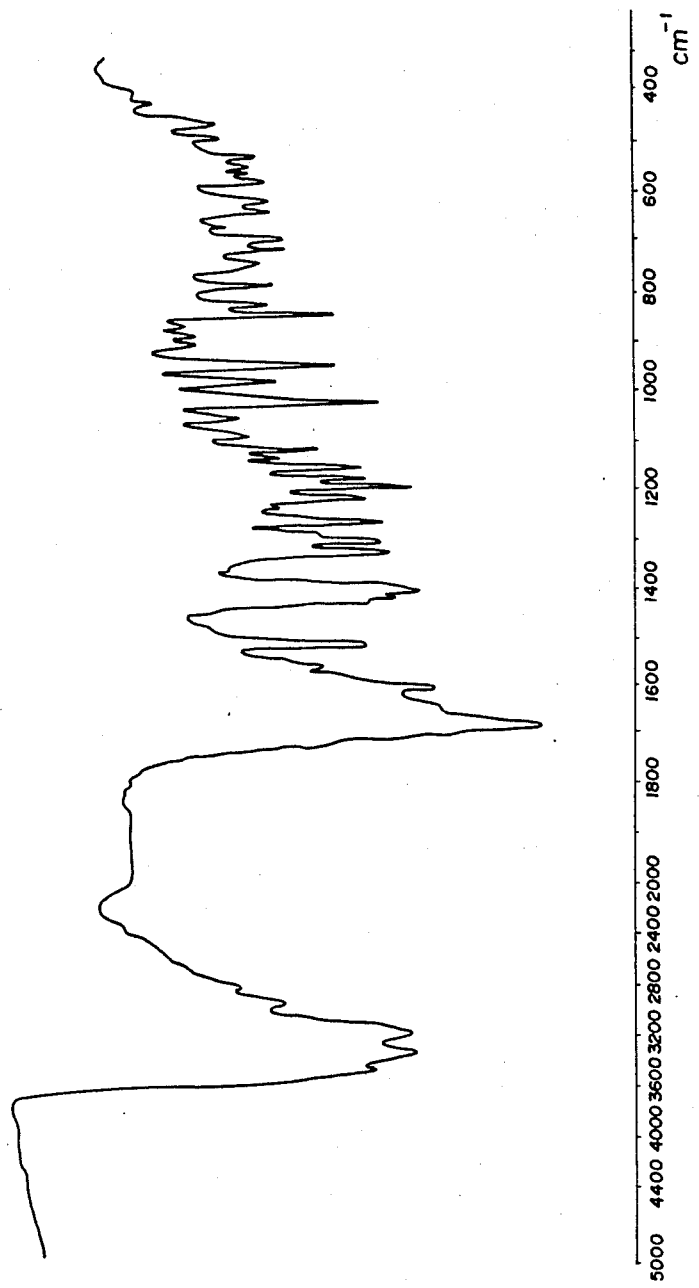
FIG. 2 shows the infrared absorption spectrum of dihydrodesoxygriseolic acid (see Example 1).
Figure 3:
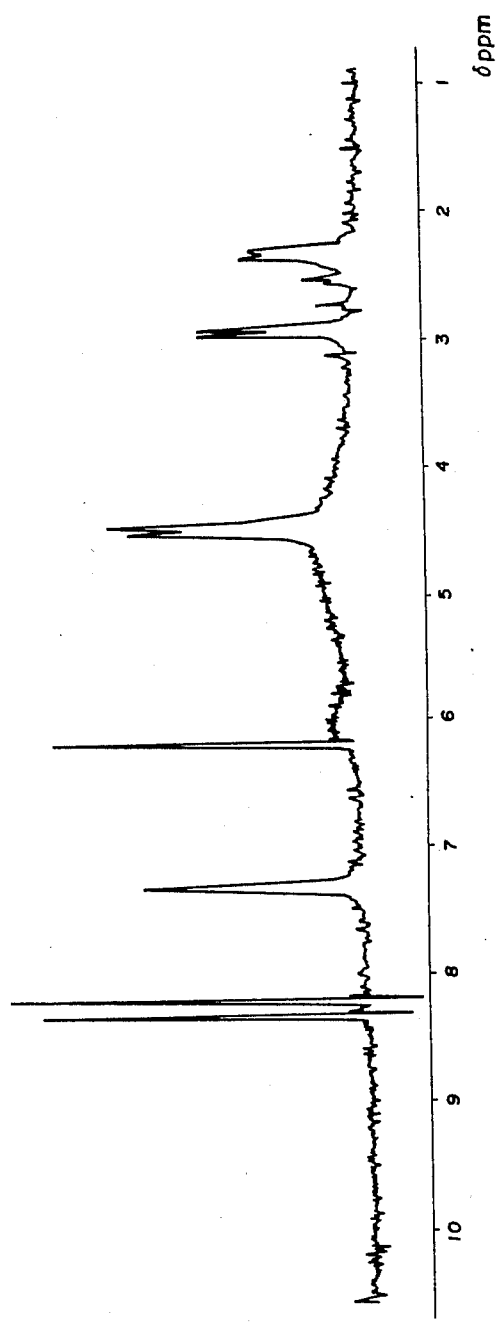
FIG. 3 shows the nuclear magnetic resonance spectrum of dihydrodesoxygriseolic acid (see Example 1).

The resulting dihydrodesoxygriseolic acid exhibited the following physical characteristics:
(1) Appearance: white plates;
(2) Melting point: 160° C. (with decomposition, accompanied by a brown discoloration);
(3) Molecular weight (by high resolution mass spectrometry): 365;
(4) Molecular formula: $C_{14}H_{15}N_5O_7$;
(5) Optical rotation: $[\alpha]^{20} = -50.7°$ (sodium D-line, c=1.0, dimethyl sulfoxide);
(6) Ultraviolet absorption spectrum (as measured in 0.01N aqueous hydrochloric acid and in 0.01N aqueous sodium hydroxide): as shown in FIG. 1 of the accompanying drawings;
(7) Infrared absorption spectrum (as measured in a KBr pellet): as shown in FIG. 2 of the accompanying drawings;
(8) $^1$H nuclear magnetic resonance spectrum (as measured at 90 MHz in hexadeuterated dimethyl sulfoxide): as shown in FIG. 3 of the accompanying drawings.

EXAMPLE 2

Sodium Dihydrodesoxygriseolate

The procedure described in Example 1 was repeated up to and including lyophilization of the aqueous solution, but using as the culture medium a medium having the composition (percentages are w/v):
Glucose 5%
Soybean Meal 1%
Yeast Extract 0.1%
Polypeptone 0.4%
Meat Extract 0.4%
Sodium Chloride 0.25%
Water to 100%
(pH 7.0 before sterilization).

Figure 4:
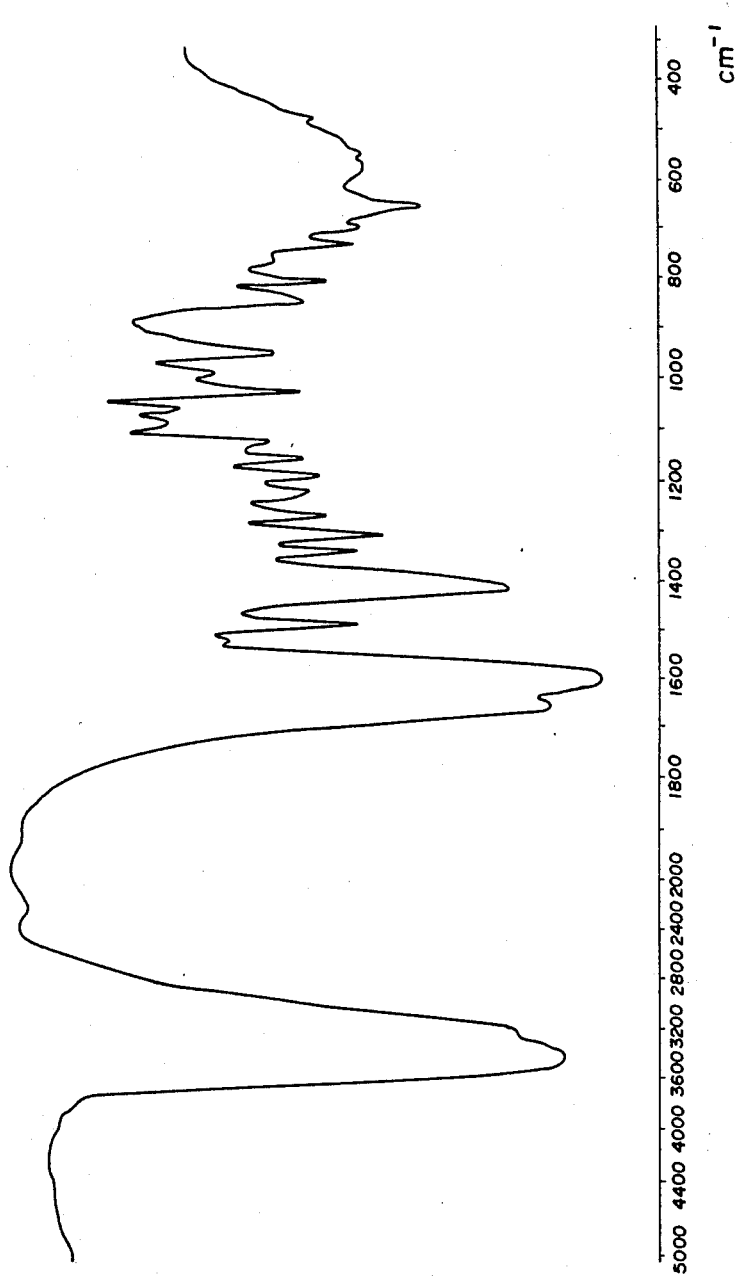
FIG. 4 shows the infrared absorption spectrum of sodium dihydrodesoxygriseolate (see Example 2).

Lyophilization gave 200 mg of crude powder. This was subjected to column chromatography through Sephadex LH-20 and the desired compound was eluted with water. Those fractions containing no griseolic acid were concentrated by evaporation under reduced pressure and left to stand overnight at 4° C. The resulting precipitate was collected by centrifugation and freeze-dried, to give 1.21 mg of sodium dihydrodesoxygriseolate having the following physical characteristics:

(1) Appearance: white powder;
(2) Melting point: 190° C. (with decomposition accompanied by a brown discoloration);
(3) Molecular formula: $C_{14}H_{13}N_5O_7Na_2$;
(4) Elemental analysis (as monohydrate): Calculated: C, 39.34%; H, 3.51%; N, 16.39%; Found: C, 38.70%; H, 3.45%; N, 16.13%;
(5) Infrared absorption spectrum (as measured in a KBr pellet): as shown in FIG. 4 of the accompanying drawings.

EXAMPLE 3

Dihydrodesoxygriseolic Acid

The procedure described in Example 1 was repeated, using the same culture medium, except that it was carried out on a larger scale. Specifically, it was carried out in a 600 liter tank containing 300 liters of culture medium. The inhibitory activity exhibited by 5 ml of the culture broth after 48 hours cultivation was found to be 80% (as calculated by the method described hereafter in Example 5). The 278 liters of filtered culture broth so obtained were separated and purified by the same procedure as described in Example 1, to give 20 mg of dihydrodesoxygriseolic acid, exhibiting a single spot on silica gel thin layer chromatography. This product was found to have physical characteristics identical with those of the product obtained as described in Example 1.

EXAMPLE 4

Sodium Dihydrodesoxygriseolate

The procedure described in Example 3 was repeated, to give 20 mg of dihydrodesoxygriseolic acid. This was suspended in a small amount of water, and then a 1N aqueous solution of sodium hydroxide was added until the pH of the mixture reached a value of 10. The suspension was then subjected to chromatography through a column of Sephadex LH-20, and the product was freeze-dried, to give 18 mg of sodium dihydrodesoxygriseolate, having physical characteristics identical with those of the product of Example 2.

EXAMPLE 5

Measurement of Enzyme Inhibitory Activity

The enzyme inhibitory activity of dihydrodesoxygriseolic acid was measured, as was that of griseolic acid itself and that of the known cAMP PDE inhibitor, papaverine, for purposes of comparison.

The test was carried out following essentially the method of A. L. Pichard and Y. U. Chung [Journal of Biological Chemistry, 251, 5726-5737 (1976)]. A crude enzymatic solution derived from rat brains was used as the source of cAMP PDE.

$^{14}C$-labeled cAMP was used as the substrate. It was employed in a 0.2M Tris-hydrochloric acid buffer solution (pH 8.0) in an amount sufficient to provide a final concentration of 0.14 μmoles. "Tris" is tris(hydroxymethyl)aminomethane. The substrate solution was mixed with an appropriate amount of the compound under test dissolved in 2-5 μl of dimethyl sulfoxide and with 20 μl of a snake venom solution and 40 μl of the crude enzyme solution. Sufficient Tris-hydrochloric acid buffer was added to make a total volume of 100 μl. The mixture was allowed to react at 30° C. for 20 minutes. At the end of this time, the reaction mixture was treated with an Amberlite (trademark) IRP-58 resin and the level of residual adenosine radioactivity in the product was determined. The experiment was carried out at a number of concentration levels of each active compound and from this was calculated the 50% inhibition value ($I_{50}$) for each test compound.

The results are shown in the following Table 1, in which the $I_{50}$ values are given in μmoles.

TABLE 1

| Test compound | $I_{50}$ (μmoles) |
|---|---|
| dihydrodesoxygriseolic acid | 0.12 |
| griseolic acid | 0.16 |
| papaverine | 3.5 |

As can be seen from the results reported in the above Table, dihydrodesoxygriseolic acid has an inhibitory activity which is comparable with that of griseolic acid; on the other hand, both griseolic acid and dihydrodesoxygriseolic acid are about 20 times as potent as the known compound, papaverine.

EXAMPLE 6

Acute Toxicity

The compounds under test were griseolic acid and dihydrodesoxygriseolic acid. The test animals were male mice of the ddY strain, 5 weeks of age and weighing 24-25 g. The mice were employed in groups of 3 or 5 animals for each test.

The compounds under test were administered at single daily doses as shown in Table 2, throughout the four days of the test. Administration was intravenous.

The results are reported in Table 2, in the form "a/b", where "a" is the number of deceased animals in the test group at the end of the test and "b" is the total number of animals in the relevant test group.

TABLE 2

| Dose (mg/kg) | Griseolic acid | Dihydrodesoxygriseolic acid |
|---|---|---|
| 100 | 3/3 | 2/3 |
| 50 | 5/5 | 0/5 |
| 25 | 4/5 | 0/5 |

TABLE 2-continued

| Dose (mg/kg) | Griseolic acid | Dihydrodesoxygriseolic acid |
| --- | --- | --- |
| 15 | 0/5 | 0/5 |

The results indicate that dihydrodesoxygriseolic acid is substantially less toxic than griseolic acid. Since the activities of the two compounds are comparable, as shown in the results of Example 5, this indicates that the range of application of dihydrodesoxygriseolic acid is likely to be substantially broader than that of griseolic acid.

We claim:

1. Dihydrodesoxygriseolic acid or a pharmaceutically acceptable alkali metal or alkaline earth metal salt or $C_1$–$C_6$ alkyl ester thereof.
2. Dihydrodesoxygriseolic acid.
3. The compound of claim 1, which is an alkali metal or alkaline earth metal salt.
4. The compound of claim 3, wherein said alkali metal salts are selected from the group consisting of sodium and potassium salts.
5. The compound of claim 3, wherein said alkaline earth metal salts are selected from the group consisting of calcium and magnesium salts.
6. Sodium dihydrodesoxygriseolate.
7. The compound of claim 1, which is a $C_1$–$C_6$ alkyl ester.
8. The compound of claim 1, wherein said ester is the methyl or ethyl ester.

* * * * *